United States Patent
Levine

(10) Patent No.: US 9,878,078 B1
(45) Date of Patent: *Jan. 30, 2018

(54) DISPOSABLE BREAST PUMP SHIELD

(71) Applicant: Sherri Levine, Bradenton, FL (US)

(72) Inventor: Sherri Levine, Bradenton, FL (US)

(73) Assignee: Momgenuity, LLC, Bradenton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/919,649

(22) Filed: Oct. 21, 2015

(51) Int. Cl.
*A61M 1/06* (2006.01)

(52) U.S. Cl.
CPC ..... *A61M 1/062* (2014.02); *A61M 2202/0014* (2013.01); *A61M 2205/07* (2013.01); *A61M 2210/1007* (2013.01)

(58) Field of Classification Search
CPC ........ A61M 1/06; A61M 1/062; A61M 1/064; A61M 1/066; A61M 1/068; A61M 2202/0014; A61M 2205/07; A61M 2202/07; A61M 2210/1007; A61J 9/08; A61J 9/085; A61J 13/00
See application file for complete search history.

(56) References Cited

U.S. PATENT DOCUMENTS

| | | | |
|---|---|---|---|
| 4,642,092 A * | 2/1987 | Moss | A61J 15/0015 604/102.03 |
| 4,799,922 A | 1/1989 | Beer et al. | |
| 5,897,580 A | 4/1999 | Silver | |
| 6,387,072 B1 | 5/2002 | Larsson et al. | |
| 6,723,066 B2 | 4/2004 | Larsson et al. | |
| 8,357,116 B2 * | 1/2013 | Simdon | A61M 1/062 604/408 |
| 8,529,501 B2 * | 9/2013 | Wach | A61M 1/06 604/119 |
| 2002/0062103 A1 | 5/2002 | Larsson et al. | |
| 2004/0074859 A1 * | 4/2004 | Hanna | A61J 9/00 215/11.1 |
| 2004/0122356 A1 | 6/2004 | Burke et al. | |
| 2011/0251552 A1 | 10/2011 | Brittner | |
| 2014/0236072 A1 * | 8/2014 | Zhang | A61M 1/06 604/23 |
| 2015/0024658 A1 * | 1/2015 | Abbott | A41C 3/14 450/39 |

FOREIGN PATENT DOCUMENTS

| | | |
|---|---|---|
| WO | 2003068291 | 8/2003 |
| WO | 2013088310 | 6/2013 |
| WO | 2013066919 | 10/2013 |

* cited by examiner

*Primary Examiner* — Nathan R Price
*Assistant Examiner* — Tasnim M Ahmed
(74) *Attorney, Agent, or Firm* — Hartman & Citrin LLC

(57) ABSTRACT

Embodiments of a breast pump shield are disclosed herein. According to various embodiments, the breast pump shield can include a body portion that has a breast engagement portion and a neck portion. The breast engagement portion can include a ring. The breast engagement portion can receive at least a portion of a breast of a user, and the neck portion can be configured to receive at least a portion of a nipple of the user and to receive milk from the breast. The breast pump shield also can include a suction chamber located in proximity to the neck portion, and a cover located at the ring of the body portion. The cover can include a support layer and a lubricant layer. The cover can provide at least part of a hermetic seal for the breast pump shield prior to use.

20 Claims, 10 Drawing Sheets

US 9,878,078 B1

DISPOSABLE BREAST PUMP SHIELD

TECHNICAL FIELD

This disclosure relates generally to breast pumps. More particularly, the disclosure made herein relates to a disposable and convenient human breast pump shield that can be easy to use, comfortable to use, and can be formed as a disposable article for purposes of convenience, sanitation, and/or other reasons.

BACKGROUND

Unless otherwise indicated herein, the details in this section are not prior art to the claims in this application and are not admitted to be prior art by inclusion in this section.

Until the middle of the twentieth century, almost all children in the world were breastfed by their mothers (or a substitute such as a wet nurse). From around the 1940's through the 1990's, the popularity and prevalence of breastfeeding decreased in the United States. In the late part of the twentieth century and over the past ten to fifteen years, breastfeeding has experienced a revival in the United States, with medical experts encouraging mothers to breastfeed children based upon a large body of scientific evidence that breastfeeding encourages healthy growth and development of children.

In modern American society, however, many mothers work outside the home or are busy with various activities that often require them to leave their homes. For many mothers, this time away from the home can be disruptive to breastfeeding schedules. Some mothers employ breast pumps to pump or express breast milk at home, at the office, or elsewhere.

Because breast milk is consumed primarily by young children, first and foremost infants of zero to six months of age and secondarily children up to about two to four years of age, some experts encourage sterilization and frequent cleaning of breast pump components. When away from the home, mothers may experience difficulty in finding a suitable place and/or equipment to thoroughly clean the breast pump components. As such, breast pumping outside the home can be difficult for mothers.

Furthermore, some women experience pain during or after breast pumping. In particular, some women experience pain as the nipples enlarge during pumping and/or from rubbing that can occur during use of a breast pump. Various approaches are used in an attempt to reduce this pain. For example, some mothers use a low setting for a breast pump at the beginning of pumping and later, after the nipple has extended and/or enlarged, the suction and/or speed of the breast pump can be increased without causing pain to the mother.

Because some breast pumps do not have variable settings, and because many mothers want to complete breast pumping as quickly as possible when away from the home, some mothers are unable to address the pain that may occur during pumping. Because of this, some mothers are discouraged from breastfeeding their children or may cease breastfeeding at the earliest opportunity.

SUMMARY

Concepts and technologies are disclosed herein for a breast pump shield. As used herein, a "breast" is used to refer only to a breast of a human female and excludes breasts of other living organisms. In some embodiments, a breast pump shield can be formed from a plastic or other material. The breast pump shield can also be formed as a disposable one-use article, as will be explained in more detail below. The breast pump shield can include a body portion and one or more covers. One or more of the covers can include multiple layers. According to various embodiments, one or more of the covers can include three layers, namely, a lubricant layer, a support layer, and a wiping layer. A layer of lubricant ("lubricant layer") also can be located within the body portion of the breast pump shield. The covers can be disposed at various locations on the breast pump shield to hermetically seal the shield from air, bacteria, dust, viruses, and/or other particles and/or liquids. Thus, the covers can cooperate with the structure of the breast pump shield to keep the inner surfaces of the breast pump shield sanitized, lubricated, and/or otherwise ready for use.

According to various embodiments, a lubricant layer can be included on the cover and/or disposed within the breast pump shield. The lubricant can be included for various purposes. In some embodiments, the lubricant can be included to reduce irritation associated with using the breast pump shield. In particular, the lubricant can be used to lubricate surfaces that come into contact with the breasts of the user and/or portions of the breasts of the user (e.g., nipples, areola, etc.). The lubricant can be formulated in a manner that prevents thinning and/or degradation of the lubricant in high heat environments (e.g., during shipping, etc.). Furthermore, the cover can include a lubricant layer for convenience of the user. For example, a user may wipe lubricant from the cover onto her breast(s) prior to use, if desired.

The support layer can be provided to support the lubricant layer and the wiping layer, as well as to provide a hermetic seal for the breast pump shield. In some embodiments, an adhesive layer may be located at a perimeter of the cover as well for purposes of joining the cover to the breast pump shield. By joining the cover to the breast pump shield and thereby providing a hermetic seal for the breast pump shield, the cover (and/or multiple covers in cooperation with one another) can be included to ensure that the breast pump shield remains sterile. The hermetic seal also may prevent leakage of, oxidation of, and/or degradation of the lubricant layer located within the body portion. Thus, as noted above, the breast pump shield can be disposable and kept sterile and ready for use by the one or more covers. The wiping layer can be included to provide a wipe or cleaner for the user. The wiping layer can be removed from the other layers, in some embodiments, and can be used to clean up before, during, or after pumping. In some embodiments, the wiping layer can include a disinfectant and/or sterilization liquid that can be wiped by the user prior to lubrication of the breast and/or before using the breast pump shield. It should be understood that this example is illustrative and therefore should not be construed as being limiting in any way.

According to some embodiments, the breast pump shield and/or components thereof can be formed from a rigid material such as an epoxy resin or other resins, plastics, thermoplastics, acrylics, rubber, synthetic rubber, other polymers or copolymers, combinations thereof, or the like. In some other embodiments, the breast pump shield and/or components thereof can be formed from semi-rigid and/or soft materials such as rubber, plastic films, latex, or the like. The materials used to form the breast pump shield can be designed to provide ample rigidity while providing a lightweight disposable article. Thus, function is balanced with cost and weight. These and other aspects of the concepts and technologies described herein will be illustrated and described herein.

According to one aspect of the concepts and technologies described herein, a breast pump shield is disclosed. The breast pump shield can include a body portion. The body portion can include a breast engagement portion and a neck portion. The breast engagement portion can include a ring, and the breast engagement portion can be configured to receive at least a portion of a human breast. The neck portion can be configured to receive at least a portion of a nipple of the human breast and to receive milk from the human breast. The breast pump shield also can include a suction chamber located in proximity to the neck portion, a hook located on the body portion, and a cover located at the ring of the body portion, wherein the cover includes a support layer and cooperates with the body portion to provide at least part of a hermetic seal for the breast pump shield prior to use.

In some embodiments, the cover further can include a lubricant layer, and the lubricant layer can include a layer of food grade lubricant. In some embodiments, the food grade lubricant can include at least one lubricant selected from a group of lubricants consisting of a coconut-based lubricant and a vegetable-based lubricant. In some embodiments, the cover further can include a lubricant layer, and the lubricant layer can include a layer of lubricant, and the breast pump shield can be disposable. In some embodiments, the lubricant can include at least one lubricant selected from a group of lubricants consisting of a mineral-oil based lubricant, a petroleum-based lubricant, and a shea-based lubricant.

In some embodiments, the cover further can include a wiping layer. In some embodiments, the wiping layer can be formed from a cotton-based fabric. In some embodiments the cover further can include a lubricant layer, the breast pump shield can be disposable, a further lubricant layer can be located within the body portion, the neck portion, and the suction chamber, and a further cover can be located over an inlet formed in the suction chamber. In some embodiments, the cover further can include a lubricant layer, the support layer can be formed from a metal foil, and the support layer can prevent leakage of the lubricant layer from the breast pump shield.

In some embodiments, the body portion can be formed from a semi-rigid material and can be configured to be disposed of after one use. In some embodiments, the hook is configured to hold a milk bag in a position at which the milk bag receives milk from the suction chamber. In some embodiments, the hook is configured to hold a bottle in a position at which the bottle receives milk from the suction chamber. In some embodiments, the breast pump shield can include another hook. The hook and the other hook can be configured to hold a milk bag in a position at which the milk bag receives milk from the suction chamber.

According to one aspect of the concepts and technologies described herein, a breast pump shield is disclosed. The breast pump shield can include a body portion. The body portion can include a breast engagement portion and a neck portion. The breast engagement portion can include a ring, the breast engagement portion can be configured to receive at least a portion of a human breast of a user, and the neck portion can be configured to receive at least a portion of a nipple of the user and to receive milk from the human breast. The breast pump shield also can include a suction chamber located in proximity to the neck portion, the suction chamber including an inlet. The breast pump shield also can include a hook located on the body portion and a first cover located at the ring of the body portion. The first cover can include a support layer and a wiping layer located in proximity to a second side of the support layer, the first cover can cooperate with the body portion to provide at least part of a hermetic seal for an interior space of the body portion prior to use, and the breast pump shield can be disposable.

In some embodiments, the first cover further can include a lubricant layer. The lubricant layer can include a layer of food grade lubricant selected from a group of lubricants consisting of a coconut-based lubricant, a flax-seed-based lubricant, a fish-oil-based lubricant, and a vegetable-based lubricant. In some embodiments, the first cover further can include a lubricant layer. The lubricant layer can include a layer of lubricant selected from a group of lubricants consisting of a mineral-oil based lubricant, a petroleum-based lubricant, and a shea-based lubricant. In some embodiments the first cover further can include a lubricant layer, a further lubricant layer can be located within the body portion, the neck portion, and the suction chamber, and a second cover can be located over an inlet formed in the suction chamber.

In some embodiments, the breast pump shield further can include an assembly structure for connecting the breast pump shield to a bottle, and a third cover located at the assembly structure. In some embodiments, the breast pump shield further can include another hook. The hook and the other hook can be configured to hold a milk bag in a position at which the milk bag receives milk from the suction chamber.

According to another aspect of the concepts and technologies described herein, a breast pump shield is disclosed. The breast pump shield can include a body portion. The body portion can include a breast engagement portion and a neck portion. The breast engagement portion can include a ring, the breast engagement portion can be configured to receive at least a portion of a human breast of a user, and the neck portion can be configured to receive at least a portion of a nipple of the user and to receive milk from the human breast. The breast pump shield also can include a suction chamber located in proximity to the neck portion. The suction chamber can include an inlet through which a breast pump can be connected to the suction chamber. The breast pump shield also can include a cover located at the ring of the body portion and two hooks located on the body portion. The hooks can be configured to hold a milk bag in a position at which the milk bag receives milk from the suction chamber, and the cover can include a support layer, a lubricant layer located in proximity to a first side of the support layer, and a wiping layer located in proximity to a second side of the support layer. The cover can cooperate with the body portion to provide at least part of a hermetic seal for an interior space of the body portion prior to use, and the breast pump shield can be disposable and configured for disposal after one use.

In some embodiments, a further lubricant layer can be located within the body portion, the neck portion, and the suction chamber; a further cover can be located over an inlet formed in the suction chamber; and the further lubricant layer can include a layer of lubricant. The lubricant can be selected from a group of lubricants consisting of a coconut-based lubricant, a flax-seed-based lubricant, a fish-oil-based lubricant, a vegetable-based lubricant, a mineral-oil based lubricant, a petroleum-based lubricant, and a shea-based lubricant.

The foregoing summary is illustrative only and is not in any way limiting. In addition to the illustrative aspects, embodiments, and features described above, further aspects, embodiments, and features will become apparent by reference to the drawings and the following detailed description.

DETAILED DESCRIPTION

Figure 1:
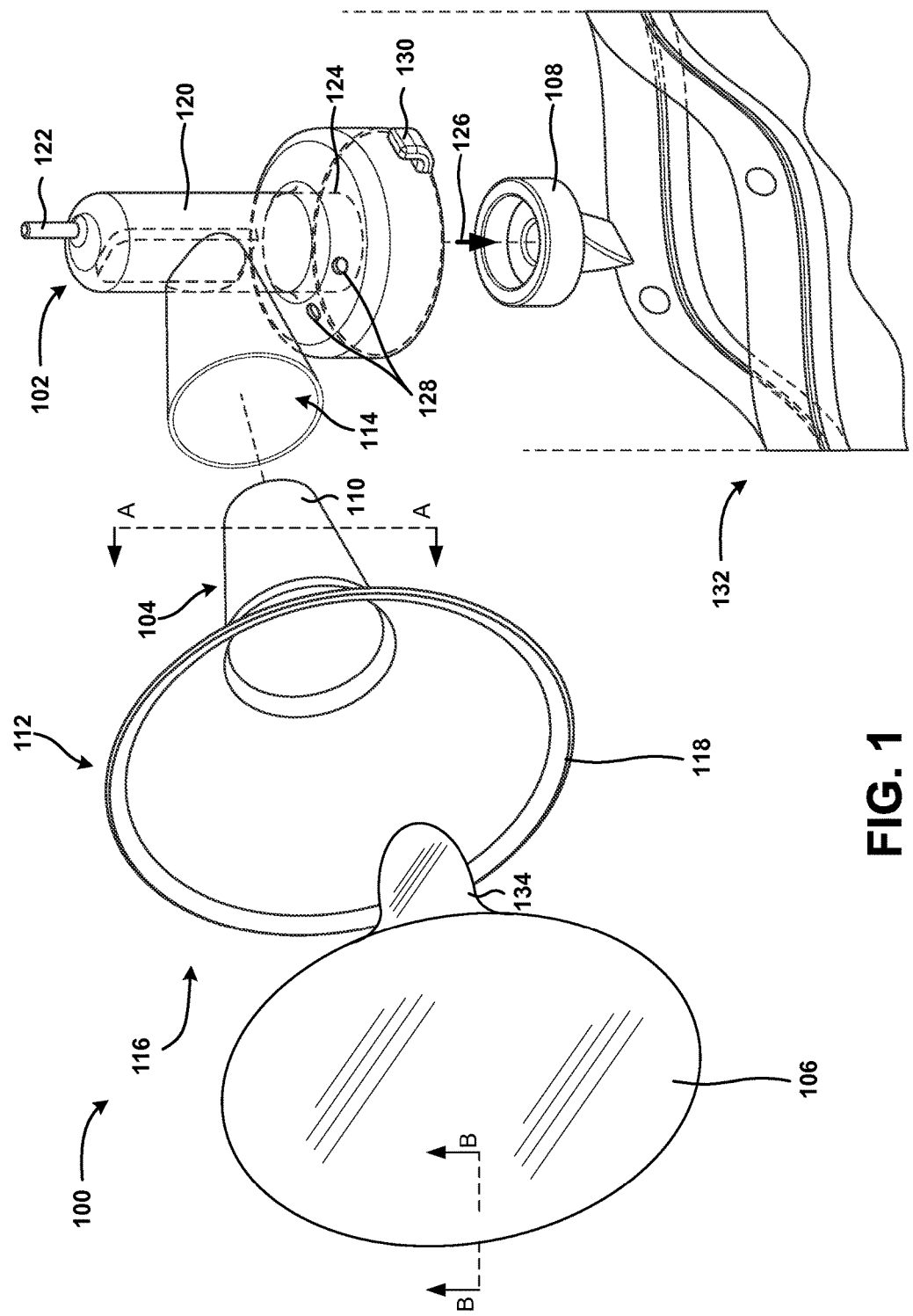
FIG. 1 is an assembly drawing of a breast pump shield, according to an illustrative embodiment of the concepts and technologies described herein.

The following detailed description is directed to a breast pump shield. A breast pump shield can be formed from a plastic or other material. The breast pump shield can also be formed as a disposable one-use article, as will be explained in more detail below. The breast pump shield can include a body portion and one or more covers. One or more of the covers can include multiple layers. According to various embodiments, one or more of the covers can include three layers, namely, a lubricant layer, a support layer, and a wiping layer. A layer of lubricant ("lubricant layer") also can be located within the body portion of the breast pump shield. The covers can be disposed at various locations on the breast pump shield to hermetically seal the shield from air, bacteria, dust, viruses, and/or other particles and/or liquids. Thus, the covers can cooperate with the structure of the breast pump shield to keep the inner surfaces of the breast pump shield sanitized, lubricated, and/or otherwise ready for use.

According to various embodiments, a lubricant layer can be included on the cover and/or disposed within the breast pump shield. The lubricant can be included for various purposes. In some embodiments, the lubricant can be included to reduce irritation associated with using the breast pump shield. In particular, the lubricant can be used to lubricate surfaces that come into contact with the breasts of the user and/or portions of the breasts of the user. The lubricant can be formulated in a manner that prevents thinning and/or degradation of the lubricant in high heat environments. Furthermore, the cover can include a lubricant layer for convenience of the user. For example, a user may wipe lubricant from the cover onto her breast(s) prior to use, if desired.

The support layer can be provided to support the lubricant layer and the wiping layer, as well as to provide a hermetic seal for the breast pump shield. In some embodiments, an adhesive layer may be located at a perimeter of the cover as well for purposes of joining the cover to the breast pump shield. By joining the cover to the breast pump shield and thereby providing a hermetic seal for the breast pump shield, the cover (and/or multiple covers in cooperation with one another) can be included to ensure that the breast pump shield remains sterile. The hermetic seal also may prevent leakage of, oxidation of, and/or degradation of the lubricant layer located within the body portion. Thus, as noted above, the breast pump shield can be disposable and kept sterile and ready for use by the one or more covers. The wiping layer can be included to provide a wipe or cleaner for the user. The wiping layer can be removed from the other layers, in some embodiments, and can be used to clean up before, during, or after pumping. In some embodiments, the wiping layer can include a disinfectant and/or sterilization liquid that can be wiped by the user prior to lubrication of the breast and/or before using the breast pump shield. It should be understood that this example is illustrative and therefore should not be construed as being limiting in any way.

According to some embodiments, the breast pump shield and/or components thereof can be formed from a rigid material such as an epoxy resin or other resins, plastics, thermoplastics, acrylics, rubber, synthetic rubber, other polymers or copolymers, combinations thereof, or the like. In some other embodiments, the breast pump shield and/or components thereof can be formed from semi-rigid and/or soft materials such as rubber, plastic films, latex, or the like. The materials used to form the breast pump shield can be designed to provide ample rigidity while providing a light-weight disposable article. Thus, function is balanced with cost and weight. These and other aspects of the concepts and technologies described herein will be illustrated and described herein.

In the following detailed description, references are made to the accompanying drawings that form a part hereof, and in which are shown by way of illustration specific embodiments or examples. It must be understood that the disclosed embodiments are merely illustrative of the concepts and technologies disclosed herein. The concepts and technologies disclosed herein may be embodied in various and alternative forms, and/or in various combinations of the embodiments disclosed herein. The word "illustrative," as used in the specification, is used expansively to refer to embodiments that serve as an illustration, specimen, model or pattern.

Additionally, it should be understood that the drawings are not necessarily to scale, and that some features may be exaggerated or minimized to show details of particular components. In other instances, well-known components, systems, materials or methods have not been described in detail in order to avoid obscuring the present disclosure. Therefore, specific structural and functional details disclosed herein are not to be interpreted as limiting, but merely as a basis for the claims and as a representative basis for teaching one skilled in the art to variously employ the present disclosure. Referring now to the drawings, in which like numerals represent like elements throughout the several figures, aspects of breast pump shields will be presented.

Referring first to FIG. 1, aspects of a breast pump shield 100 according to various embodiments of the concepts and technologies described herein will be described in detail. In particular, FIG. 1 illustrates one illustrative embodiment of a breast pump shield 100. It should be understood that the illustrated and described illustrative embodiment of the breast pump shield 100 shown in FIG. 1 is one illustrative embodiment of the concepts and technologies described herein, and therefore should not be construed as being limiting in any way of the concepts and technologies described herein.

In some embodiments, as shown in FIG. 1, a breast pump shield 100 can include a breast pump shield main body portion ("body portion") 102, a funnel portion 104, a cover 106, and a valve attachment 108. The funnel portion 104 can be shaped to receive and/or engage a breast during lactation. According to various embodiments of the concepts and technologies described herein, the funnel portion 104 can include a neck portion 110 and a breast engagement portion 112. According to various embodiments, the neck portion 110 can be received by a funnel insertion portion 114 of the body portion 102.

Thus, it can be appreciated that the body portion 102 can be configured to act as a backbone of sorts of the breast pump shield 100. Thus, the body portion 102 can be designed to support other components of the breast pump shield 100. As will be illustrated and described in more detail below, the body portion 102 can have various configurations and/or features. As such, the illustrated and described example embodiment shown in FIG. 1 is merely illustrative of the concepts and technologies described herein and should not be construed as being limiting in any way.

According to various embodiments, the funnel portion 104 can be connected to the body portion 102 via a connection mechanism formed at the neck portion 110 and the funnel insertion portion 114. In some embodiments, the connection mechanism can include a pressure fit formed between the neck portion 110 and the funnel insertion portion 114. Thus, it can be appreciated that at least a portion of the outside diameter of the neck portion 110 can be slightly larger than at least a portion of the inside diameter of the funnel insertion portion 114, though this is not necessarily the case. Although not shown in FIG. 1, it should be understood that the neck portion 110 and/or the funnel insertion portion 114 can include ribs, threads, and/or other structures to create a connection between the body portion 102 and the funnel portion 104 and/or for other purposes. It should be understood that this example is illustrative and therefore should not be construed as being limiting in any way.

The breast engagement portion 112 of the funnel portion 104 can be shaped and/or configured to receive and/or engage an outer surface of a breast of a user. The breast engagement portion 112 also can be configured to center a nipple of the breast within the breast engagement portion 112 during lactation/suction and/or to encourage the nipple of the breast to enter a suction and/or stimulation chamber, as will be explained in more detail below. It can be appreciated that during lactation, the nipple of the user may enlarge and move into the inside of the neck portion 110 and/or the funnel insertion portion 114. It should be understood that this example is illustrative and therefore should not be construed as being limiting in any way.

According to various embodiments, a breast or a portion thereof can be inserted into the breast engagement portion 112 via an open end 116. The open end 116 can be defined, in some embodiments, by a ring 118 of material located at the open end 116. The ring 118 can engage the breast or chest of the user and the breast or areola of the user can be engaged within the breast engagement portion 112, or a portion thereof. The nipple of the breast can pass through the breast engagement portion 112 and into a stimulation and/or suction chamber or region formed by the neck portion 110, as noted above. In the illustrated embodiment, the stimulation chamber or region is provided by a neck portion 110 and the funnel insertion portion 114 as explained above. It should be understood that this example is illustrative and therefore should not be construed as being limiting in any way.

As mentioned above, the neck portion 110 can be configured to accommodate and/or engage the nipple during lactation. Thus, although not shown in FIG. 1, an inside surface of the neck portion 110 can include ribs, ridges, and/or other structures to stimulate milk production and/or lactation during use of the breast pump shield 100. In various embodiments, the neck portion 110 can be configured as a cylindrical passageway. The neck portion 110 can be tapered, in some embodiments, though this is not necessarily the case. During pumping, the nipple can extend to or even into the neck portion 110.

According to various embodiments, the extension of the nipple into, through, or within the neck portion 110 can occur repeatedly with the application of suction to the neck portion 110. The movement and/or extension of the nipple within the neck portion 110 can encourage and/or stimulate milk flow, as generally is understood. The body portion 102 also can include a suction chamber, structure, or region ("suction chamber") 120. Air pressure within the suction chamber 120 can be controlled and/or regulated by a breast pump (not visible in FIG. 1), which can be connected to the suction chamber 120 via a hose, connector, or other structure. The hose, connector, or other structure can be connected to or inserted into the suction chamber 120 via an inlet 122. Thus, the breast pump or other device can control air pressure within the suction chamber 120, the neck portion 110, and/or the breast engagement portion 112 via connection through the inlet 122.

The suction chamber 120 also can be formed by a valve attachment 108. The valve attachment 108 can attach to a ring 124 formed as part of the body portion 102. As is generally understood, the valve attachment 108 can be configured to allow one-way fluid flow from within the suction chamber 120 to outside of the suction chamber 120. Specifically, a fluid (e.g., air, milk, etc.) can flow from within the suction chamber 120 to outside of the valve attachment 108 along a flow path 126, but fluid (e.g., air, milk) cannot flow back into the suction chamber 120 from outside of the valve attachment (against the flow path 126). Thus, the breast pump shield 100 can be shaped and configured to prevent reverse flow of milk, air, and/or contaminants from within the suction chamber 120 to a hose or other structure connected to the inlet 122. It should be understood that this example is illustrative and therefore should not be construed as being limiting in any way.

The body portion 102 also can include one or more vents 128. The vents 128 can be positioned outside of the ring 124. Thus, if a bottle (not shown in FIG. 1) or bag is attached to the body portion 102, the vents 128 can allow air pressure to escape from within the bottle or bag, thereby allowing fluid to more easily flow into the bottle or bag than would be possible without the vents 128. It should be understood that this example is illustrative and therefore should not be construed as being limiting in any way.

According to various embodiments, the body portion 102 and/or one or more portions thereof can include a lubricant layer (not visible in FIG. 1). In the illustrated embodiment, at least portions of the breast engagement portion 112 and the neck portion 110 include the lubricant layer. In some embodiments, the suction chamber 120, the inlet 122, other portions of the breast pump shield 100 and/or portions thereof can include the lubricant layer. The lubricant layer will be illustrated and described in more detail below. Additionally, the cover 106 will be illustrated and described in more detail below.

Figure 8:
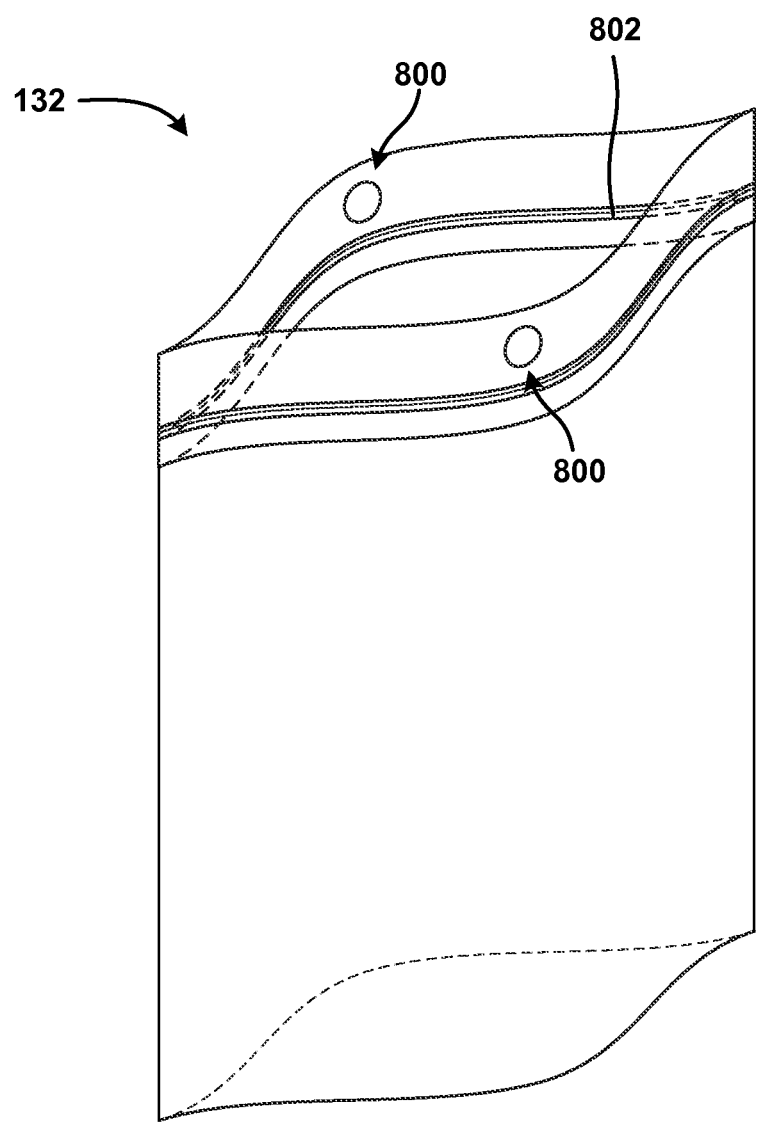
FIG. 8 is a perspective view of a milk bag for use with a breast pump shield, according to an illustrative embodiment of the concepts and technologies described herein.

According to various embodiments, the body portion 102 also can include one or more hooks 130. While only one hook 130 is visible in FIG. 1 (a second hook 130 is out of view), it should be understood that one, two, three, or more than three hooks 130 can be included on the breast pump shield 100. The hooks 130 can be used to hold, position, and/or retain a bag or other receptacle ("milk bag") 132 at a location at which milk from the suction chamber 120 can flow into the milk bag 132. Another view of the milk bag 132 is shown in FIG. 8.

In some embodiments, the hooks 130 can be used to hold a retention mechanism such as a rubber band, elastic band, clip, or the like, which can be used to retain a bottle in position without requiring threads on the inside of the body portion 102. Thus, it can be appreciated that the body portion 102 can be configured for use with bags and bottles of various configurations, thereby enabling universal (or nearly universal) use of the breast pump shield 100 with bottles, bags, and/or other milk receptacles.

Components of the breast pump shield 100 can be formed from various materials. According to various embodiments, the body portion 102 of the breast pump shield 100 and/or components of the body portion 102 such as the breast engagement portion 112, the ring 118, the neck portion 110, and/or the suction chamber 120 can be formed from one or more plastics, one or more thermoplastics, one or more acrylics, one or more resins, one or more polymers or copolymers, other (non-plastic and non-polymer) materials, and/or combinations thereof. According to some embodiments, the body portion 102 of the breast pump shield 100 can be formed using various manufacturing processes such as injection molding processes, three dimensional printing processes, machining processes, forging processes, combinations thereof, or the like. The material used to form the breast pump shield 100 can be lightweight yet rigid, thereby reducing weight, cost, and waste associated with the breast pump shield 100. The breast pump shield 100 can be disposable and designed for a single use. Because other materials and/or processes can be used to form the body portion 102 and/or other components of the breast pump shield 100, it should be understood that these examples are illustrative and therefore should not be construed as being limiting in any way.

In some embodiments, as can be seen in FIG. 1, the cover 106 can include a finger grip, tab, protrusion, or other structure ("tab") 134. The tab 134 can be used to provide a grip for a user to grasp the cover 106. Using the tab 134, the user can detach the cover 106 from the breast pump shield 100. It can be appreciated that in various embodiments, the cover 106 can be attached to the breast pump shield 100 using an adhesive. Thus, the cover 106 can be peeled away from the breast pump shield 100, in some embodiments, as generally is understood. Because the tab 134 can be optional and/or can be replaced by additional and/or alternative structures or devices, the tab 134 is not shown in the other FIGURES. It should be understood that the tab 134 or other structures or devices can be included in some, all, or none of the illustrated embodiments, and as such, the illustrated embodiments that omit the tab 134 are merely illustrative and should not be construed as being limiting in any way.

In some embodiments, the cover 106 can be configured such that the cover 106 can enwrap the entire breast pump shield 100 or a component thereof. For example, in some embodiments, the cover 106 can enwrap the entire breast pump shield 100, the entire body portion 102, the entire neck portion 110, and/or other components of the breast pump shield 100. In some embodiments, the components of the breast pump shield 100 can be enwrapped or enclosed by the cover 106 and/or multiple covers 106, so a user can unwrap the components and assemble the sterile and lubricated components together. For example, the cover 106 can be located at the ring 118, and the entire breast pump shield 100 can then be enclosed in an outer wrapper (e.g., a plastic or cellophane bag, etc.). In some other embodiments, the entire breast pump shield 100 can be unwrapped, and then can be used as a sterile and lubricated breast pump shield. Thus, the embodiments shown in the FIGURES, wherein the cover 106 covers only a portion of the breast pump shield 100 should be understood as being illustrative of some contemplated embodiments and should not be construed as being limiting in any way.

The breast pump shield 100 shown in FIG. 1 has been described as including one cover 106, one breast engagement portion 112, one neck portion 110, one suction chamber 120, one inlet 122, and two hooks 130. It should be understood, however, that some embodiments of the breast pump shield 100 can include zero, one, or more than one cover 106; zero, one, or more than one suction chamber 120; zero, one, or more than one inlet 122; and/or zero, one, two, or more than two hooks 130. In one contemplated embodiment, for example, the breast pump shield 100 can include a truncated breast engagement portion or can omit the breast engagement portion 112 altogether, thereby resulting in a short and compact breast pump shield 100 that essentially consists of the neck portion 110 and the suction chamber 120. It should be understood that this example is illustrative and therefore should not be construed as being limiting in any way.

Figure 3:
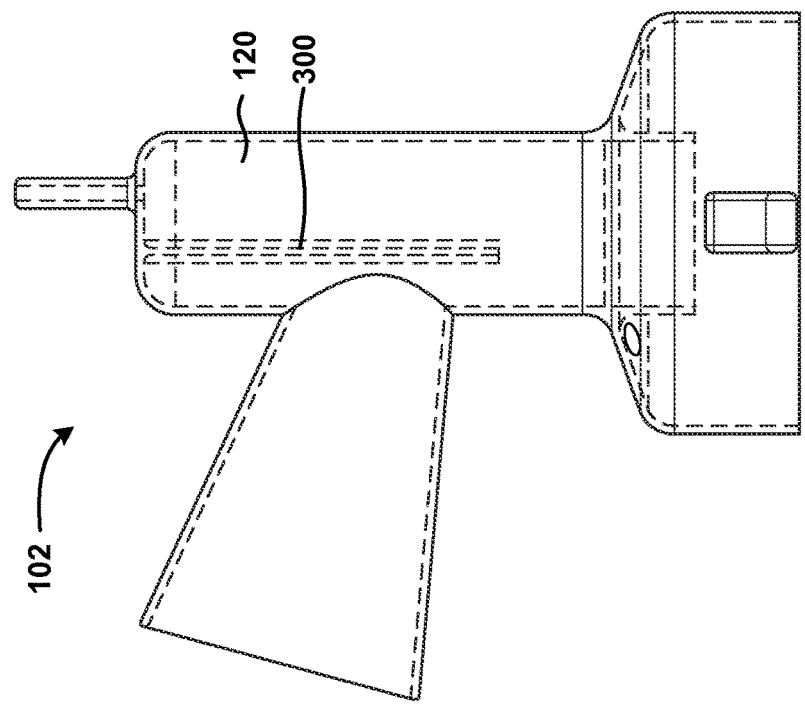
FIG. 3 is a side view of a body portion of a breast pump shield, according to an illustrative embodiment of the concepts and technologies described herein.
Figure 2:
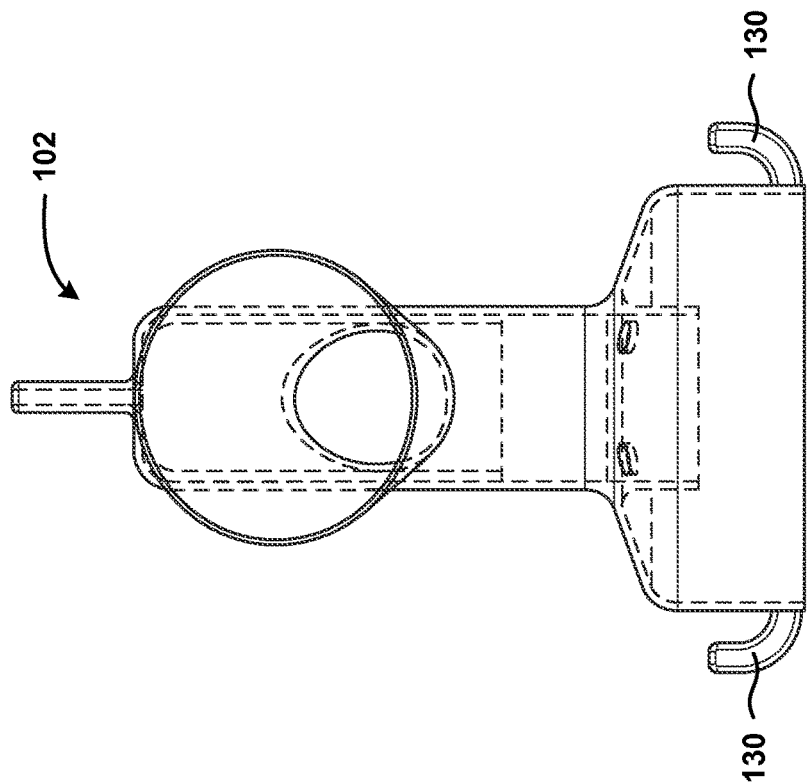
FIG. 2 is a front view of a body portion of a breast pump shield, according to an illustrative embodiment of the concepts and technologies described herein.
Figure 4:
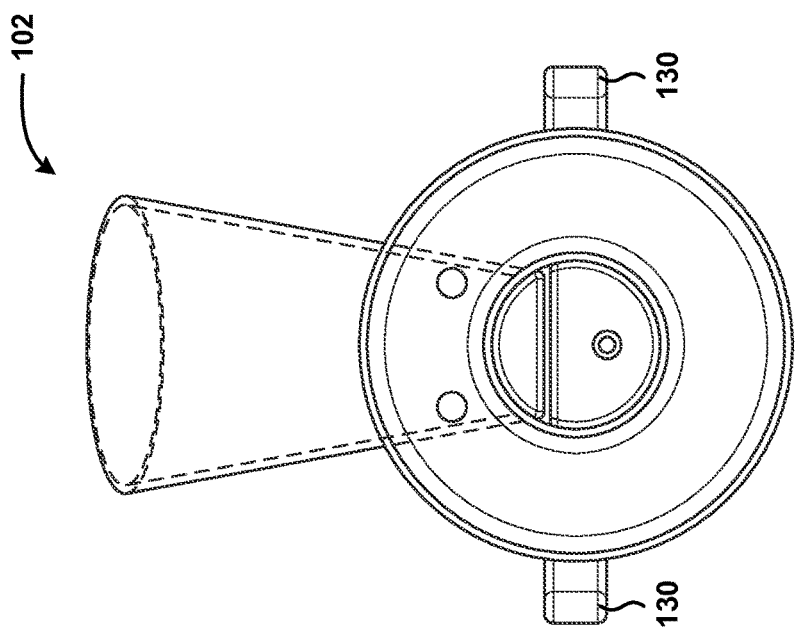
FIG. 4 is a bottom view of a body portion of a breast pump shield, according to an illustrative embodiment of the concepts and technologies described herein.

FIGS. 2-4 illustrate additional views of the body portion 102 of the breast pump shield 100. These views are provided to illustrate additional details of the structure of the body portion 102, most of which has been discussed above with reference to FIG. 1. As visible in FIG. 3, the suction chamber 120 of the body portion 102 can be divided or sectioned by a divider 300. The divider 300 can prevent milk from squirting out of the breast and into a proximity of the inlet 122, from which location the milk could more easily enter the inlet 122 and/or a hose attached to the inlet 122. Thus, the divider 300 can be included to reduce the chances of contamination of the breast pump hose (not visible in the FIGURES) and/or other structures. It should be understood that this example is illustrative and therefore should not be construed as being limiting in any way.

Figure 5:
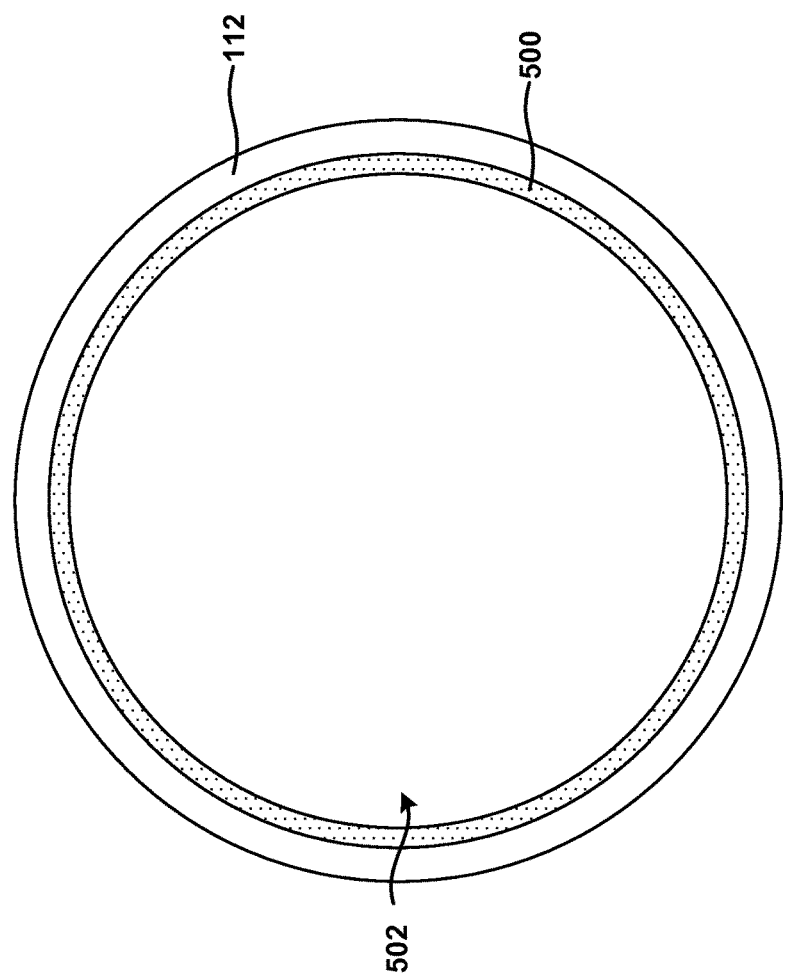
FIG. 5 is a line drawing illustrating additional features of a breast pump shield, according to some illustrative embodiments of the concepts and technologies described herein.

Turning now to FIG. 5, additional aspects of the concepts and technologies described herein for a breast pump shield will be described in detail. In particular, FIG. 5 is a line drawing illustrating cut-away view of the neck portion 110 of the breast pump shield 100 as viewed from the cut-line A-A shown in FIG. 1, according to some illustrative embodiments of the concepts and technologies described herein. It should be understood that this example is illustrative and therefore should not be construed as being limiting in any way.

As can be seen in FIG. 5, the neck portion 110 can include a lubricant layer 500 disposed within the neck portion 110. In some embodiments, the lubricant layer 500 can be located between an inner surface (not labeled in FIG. 5) of the neck portion 110 and a void 502 of the neck portion 110. As mentioned above, it can be appreciated that the void 502 can accommodate a nipple of a lactating mother during pumping and/or use of the breast pump shield 100. As such, in some embodiments the lubricant layer 500 can be included to lubricate the inner surface of the neck portion 110. The lubricant layer 500 can be included to prevent irritation of the nipples, which can result from pumping. Similarly, the lubricant layer 500 can be included to reduce pain, which some women may experience when pumping. Still further, the lubricant layer 500 can be included to allow the nipple to slide up and down along the side wall of the neck portion 110, which can stimulate the nipples and encourage milk flow. It should be understood that these examples are illustrative and therefore should not be construed as being limiting in any way.

The functionality of the lubricant layer 500 can be provided, in some embodiments, by a food grade and/or hypoallergenic lubricant. Thus, the lubricant layer 500 can be safe for use during lactation as any amounts (trace or otherwise) that pass into the expressed or pumped breast milk may not pose a risk to an infant, toddler, or other child or children who consume the milk produced using the breast pump shield 100. According to one contemplated embodiment, the lubricant used to provide the lubricant layer 500 can include a coconut-based lubricant. According to another contemplated embodiment, the lubricant used to provide the lubricant layer 500 can include a palm-based lubricant. According to another embodiment, the lubricant used to provide the lubricant layer 500 can include a fruit-based or vegetable-based lubricant such an olive-oil-based lubricant, a vegetable-oil-based lubricant (e.g., canola oil, soy oil, peanut oil, corn oil, avocado oil, safflower oil, sunflower oil, etc.), nut oils (e.g., almond oil, walnut oil), other oils (e.g., cottonseed oil, sunflower oil, etc.) combinations thereof, or the like. According to other embodiments, the lubricant used to provide the lubricant layer 500 can include other oils and/or lubricants such as petroleum based and/or mineral-based lubricants. According to still other embodiments, the lubricant used to provide the lubricant layer 500 can include flax oil or fish oil, which can be high in Omega-5 fatty acids that are known to encourage healthy brain development of infants. Thus, oil that leaks into the milk can actually be beneficial for the infant, in some embodiments. Because other oils and/or lubricants can be used, it should be understood that the above examples are illustrative and therefore should not be construed as being limiting in any way.

According to various embodiments, the lubricant layer 500 can be provided by a thick heat-resistant lubricant. As such, during shipping and/or other transportation of the breast pump shield 100, the lubricant layer 500 may not move or run from an original location. This functionality can be particularly useful when shipping the breast pump shield 100 in a high heat environment, or the like. As such, the breast pump shield 100 can be ready for use without applying lubricant to the breast pump shield 100, a component thereof, and/or a nipple or breast of the lactating mother. In some embodiments, the lubricant or oil used to provide the lubricant layer 500 can be thickened using various processes to prevent running and/or melting of the lubricant. It should be understood that this example is illustrative and therefore should not be construed as being limiting in any way.

Figure 6A:
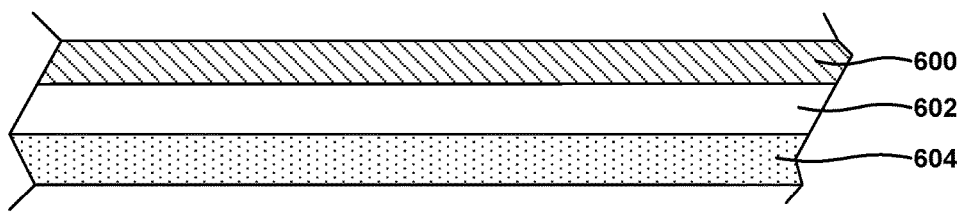
FIGS. 6A-6B are line drawings illustrating additional features of a breast pump shield cover, according to some illustrative embodiments of the concepts and technologies described herein.
Figure 6B:
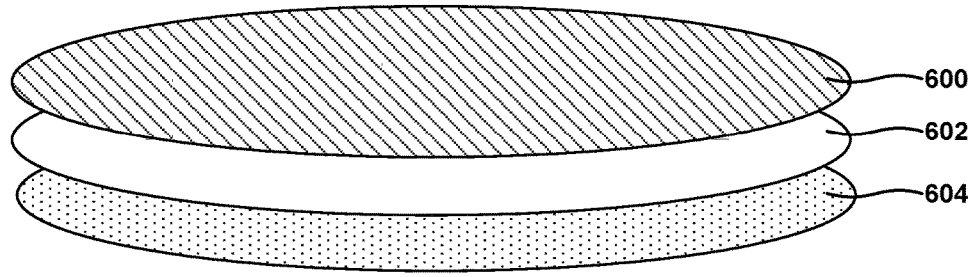

Referring now to FIGS. 6A-6B, additional aspects of the concepts and technologies described herein for a breast pump shield 100 will be described in detail. In particular, FIG. 6A illustrates a cross section of the cover 106, viewed along the cut/view line B-B shown in FIG. 1. It can be appreciated that a cross section view of any portion of the cover 106 can be substantially similar to the view shown in FIG. 6A. Additionally, FIG. 6B illustrates an assembly drawing of the cover 106. Collective reference will be made to FIGS. 6A-6B to describe the cover 106 and/or the components thereof.

As shown in FIGS. 6A-6B, the cover 106 can include multiple layers. According to various embodiments of the concepts and technologies described herein, the cover 106 can include two or more layers. According to some other embodiments, the cover 106 can include three or more layers. In the illustrated embodiment, the cover 106 includes three layers. Based upon the foregoing, it can be appreciated that the illustrated embodiment is illustrative and therefore should not be construed as being limiting in any way.

The cover 106 shown in FIGS. 6A-6B includes a wiping layer 600, a support layer 602, and a lubricant layer 604. According to various embodiments, the lubricant layer 604 can be provided by a lubricant that may be similar or even identical to the lubricant layer 500 illustrated and described above with reference to FIG. 5, though this is not necessarily the case. Thus, it can be appreciated that according to some embodiments of the concepts and technologies described herein, the lubricant layer 604 can be provided by a coconut-based lubricant, a palm-based lubricant, a shea-based lubricant, a petroleum-based lubricant, a nut-based lubricant, a fruit-based lubricant, a vegetable-based lubricant, a mineral-oil-based lubricant, other oils and/or lubricants, combinations thereof, or the like. Because the lubricant layer 604 can be provided by other lubricants, it should be understood that the above examples are illustrative and therefore should not be construed as being limiting in any way.

In some embodiments, the lubricant layer 604 can be thickened as explained above with reference to the lubricant layer 500. The lubricant layer 604 can be applied by a user to her nipples, areolas, and/or other parts of her breast to reduce friction, rubbing, and/or pain associated with pumping the breasts during milk production. As noted above, the lubricant layer 604 can be included to obviate the user from needing additional lubricant. As such, it can be appreciated that the lubricant layer 604 can be included to provide extra lubricant that may or may not be used by a user. In still other embodiments, the cover 106 can include the lubricant layer 604 so a user can rub the cover on the breasts and/or parts of the breast or on the breast pump shield 100 and/or components thereof to further lubricate the breasts and/or breast pump shield 100 as described herein. It should be understood that this example is illustrative and therefore should not be construed as being limiting in any way.

The support layer 602 can be provided to add strength and/or support to the cover 106, in some embodiments. In particular, in some embodiments, the support layer 602 can be provided by a layer, sheet, or piece of a metal foil, a plastic sheet, a polymer layer, and/or another substrate or material. In addition and/or instead of providing rigidity and/or support for the cover 106, the support layer 602 can, in some embodiments, provide a hermetic seal for the breast pump shield 100 to keep the breast pump shield sanitary and/or sterile. The support layer 602 also can be configured to prevent leakage of, oxidation of, and/or other degradation of the lubricant layer 500 and/or the lubricant layer 604 if illustrated and described herein. In one contemplated embodiment, the support layer 602 is provided by a metal foil layer. It should be understood that this example is illustrative and therefore should not be construed as being limiting in any way.

According to some embodiments, the wiping layer 600 can be provided by a natural or synthetic fiber cloth layer. In particular, some embodiments of the wiping layer 600 include a cotton fiber layer, while some other embodiments of the wiping layer 600 are provided by synthetic fiber layer. The wiping layer 600 can be included for the convenience of the user.

In particular, the wiping layer 600 can be used as a napkin, towel, or the like, for cleaning the breast before, during, or after pumping. For example, the wiping layer 600 can be used to wipe lubricant off of the breast, to wipe milk off of the breast, to clean hands, fingers, or the like, and/or to wipe or clean other surfaces. In some contemplated embodiments, the wiping layer 600 can be joined to the support layer 602 using an adhesive. As such, in some embodiments a user can peel the wiping layer 600 away from the support layer 602. It can be appreciated that the support layer 602 can prevent the wiping layer 600 from absorbing and/or touching the lubricant layer 604. It should be understood that these examples are illustrative and therefore should not be construed as being limiting in any way.

It can be appreciated from the above description of the cover 106 that the breast pump shield 100 can be ready for use. Thus, some embodiments of the concepts and technologies described herein are used to provide a disposable and/or travel breast pump shield 100 that does not require cleaning prior to use for pumping. Furthermore, embodiments of the concepts and technologies described herein provide a sterile and ready to use breast pump shield that requires no additional cleaning and/or lubrication prior to or after use, thereby providing a truly portable and/or disposable breast pump shield 100. It should be understood that these examples are illustrative and therefore should not be construed as being limiting in any way.

Although not visible in the FIGURES, it should be understood that the cover 106 and/or other covers for the breast pump shield 100 can include an adhesive layer. The adhesive layer can be disposed on the support layer 602 and/or on other layers or portions of the cover 106. In some contemplated embodiments, the adhesive is disposed about a ring of the support layer 602. In some embodiments, the adhesive can be disposed in a ring that substantially corresponds to a location of the ring 118 shown in FIG. 1. In some embodiments, the lubricant layer 604 does not extend to or onto the adhesive layer. Thus, the lubricant layer 604 can be configured not to interfere with the adhesive layer, in some embodiments. In some embodiments, the adhesive layer is releasable and/or re-sealable. Thus, some embodiments of the adhesive layer can allow the user to attach and/or detach the cover 106 from the breast pump shield 100. It should be understood that these examples are illustrative and therefore should not be construed as being limiting in any way.

Figure 7:
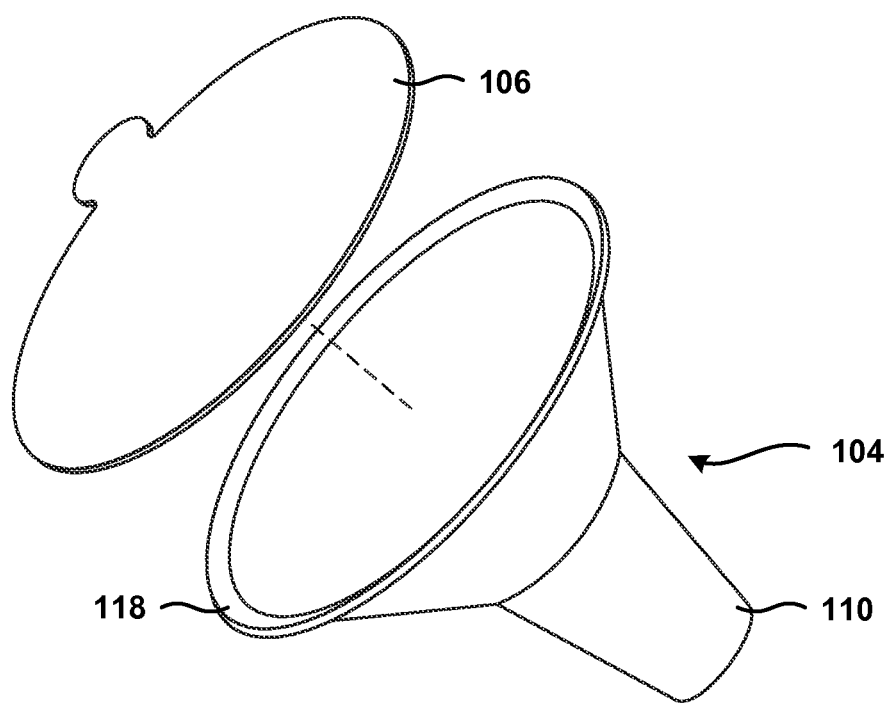
FIG. 7 is a perspective view of a funnel portion and cover of a breast pump shield, according to an illustrative embodiment of the concepts and technologies described herein.

FIG. 7 illustrates an assembly drawing of a cover 106 and a funnel portion 104. The cover 106 can be disposed to the ring 118 of the funnel portion 104, as mentioned above with reference to FIG. 1. Although not shown in FIG. 7, it should be understood that another cover can be located at the opposite end of funnel portion 104 (e.g., at the end if the neck portion 110), thereby sealing the funnel portion 104 and providing the funnel portion 104 with a hermetic seal. Furthermore, as explained above with reference to FIG. 1, a lubricant can be located within the funnel portion 104, if desired.

FIG. 8 illustrates a perspective view of a milk bag 132 according to one illustrative embodiment of the concepts and technologies described herein. As can be seen in FIG. 8, the milk bag 132 can include apertures 800. The apertures 800 can be used to connect the milk bag 132 to the hooks 130 of the body portion 102. This can conveniently locate the milk bag 132 in a position at which milk can be received without requiring screwing a bottle onto the body portion 102 and/or other structures. As shown in FIG. 8, the milk bag can include a seal 802. According to various contemplated embodiments, the seal 802 can be provided by a zip-style seal, mechanical fasteners, adhesives, heat-activated seals, combinations thereof, or the like. The seal 802 can be used to seal the milk bag 132 after pumping to prevent spillage and/or leakage of the milk in the milk bag 132. It should be understood that these examples are illustrative and therefore should not be construed as being limiting in any way.

Figure 9:
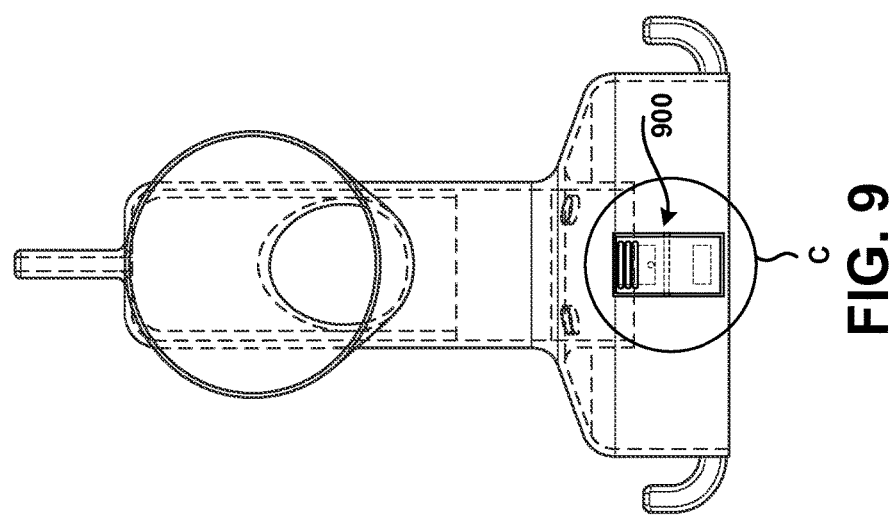
FIG. 9 is a line drawing illustrating additional features of a breast pump shield, according to some other illustrative embodiments of the concepts and technologies described herein.

Turning now to FIG. 9, additional aspects of the concepts and technologies described herein will be described. In particular, FIG. 9 shows an example embodiment of a universal or nearly-universal bottle thread attachment mechanism ("thread attachment mechanism") 900. Although the body portion 102 is illustrated in FIG. 9 as including only one thread attachment mechanism 900, it should be understood that the body portion 102 can include multiple thread attachment mechanisms 900. In one contemplated embodiment, for example, four thread attachment mechanisms 900 are distributed radially around the body portion 102 (e.g., one or more the hooks 130 can be substituted for the thread attachment mechanisms 900 and/or the thread attachment mechanisms 900 and the hooks 130 can both be distributed radially and therefore may both be included). According to one embodiment, two hooks 130 are located as shown in FIG. 9 (e.g., distributed radially one hundred eighty degrees apart), and the thread attachment mechanisms can be distributed radially (ninety degrees apart and forty five degrees offset from the hooks 130). It should be understood that this example is illustrative and therefore should not be construed as being limiting in any way.

Figure 10:
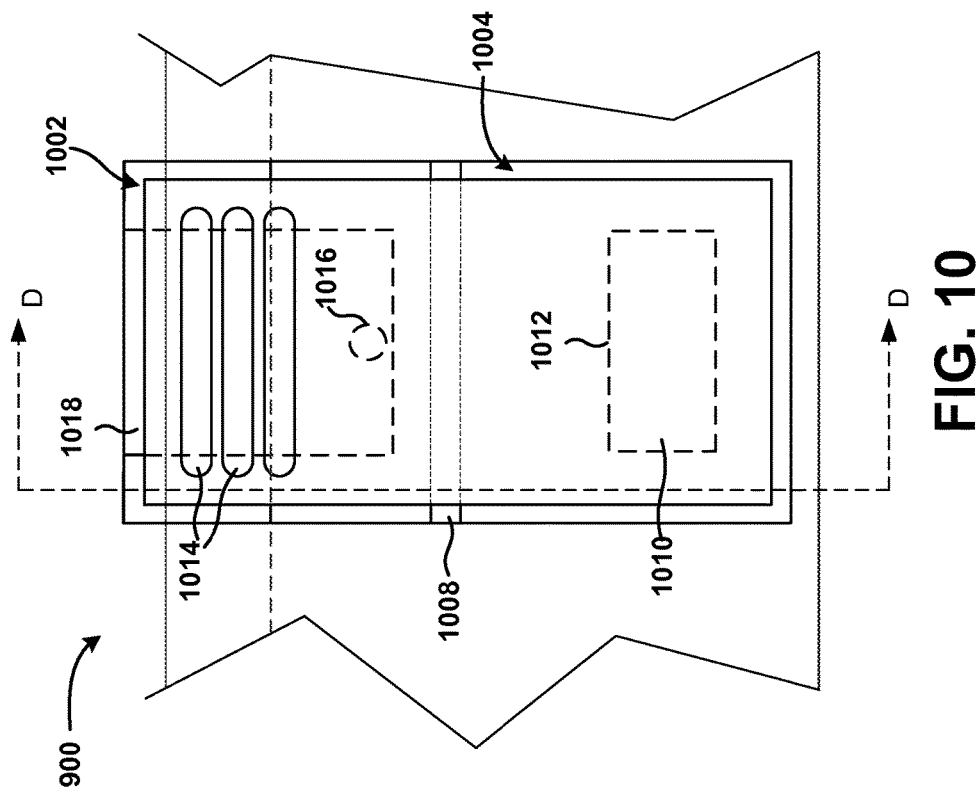
FIG. 10 is an expanded view of a universal thread attachment mechanism for a breast pump shield, according to an illustrative embodiment of the concepts and technologies described herein.
Figure 11:
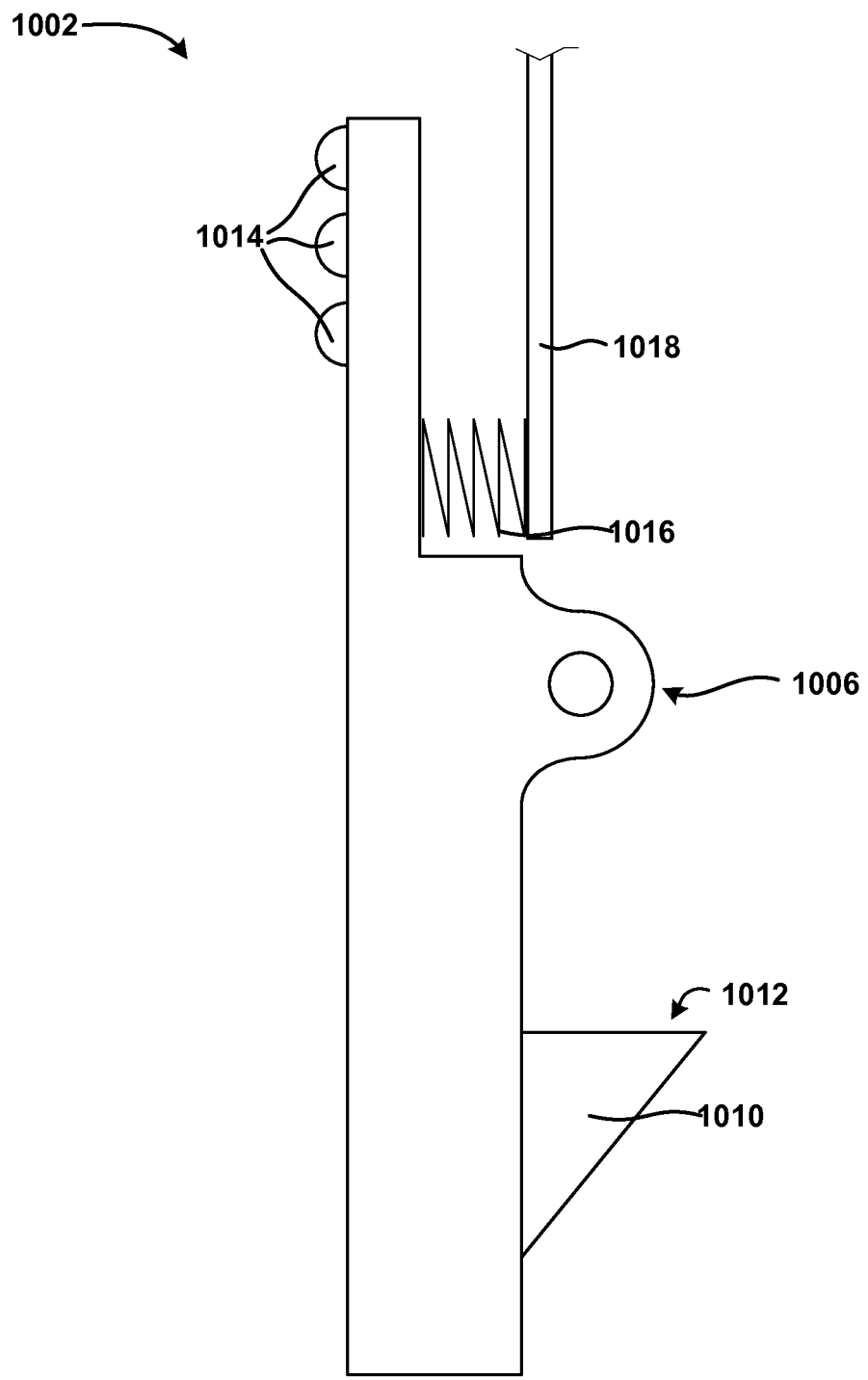
FIG. 11 is a line drawing showing additional features of the universal thread attachment mechanism as viewed along view line D-D in FIG. 10, according to an illustrative embodiment of the concepts and technologies described herein.

In some embodiments, the thread attachment mechanism 900 can be spring loaded, as will be more clearly understood with reference to FIGS. 10-11. In some other embodiments, the thread attachment mechanism 900 may not be spring loaded. In yet other embodiments, the thread attachment mechanism 900 can be provided with spring by the material used to form the breast pump shield 100 and as such, separate springs may not be included. It should be understood that these examples are illustrative and therefore should not be construed as being limiting in any way.

It should be understood that the illustrated embodiment of the thread attachment mechanism 900 is only one contemplated embodiment of a suitable structure for connecting the breast pump shield 100 to a bottle or other receptacle. Other contemplated embodiments include the use of a thread adapter that can be provided to connect one type of threads to another type of threads. Such a thread adapter may screw onto or into threads formed on the body portion 102 and/or otherwise connect to the body portion 102 (e.g., to the hooks 130). Such adapters can be included with the breast pump shield 100 and can be disposable, if desired. In another contemplated embodiment, adhesives, elastic connectors, pressure fits, and/or other structures and/or devices can be used to provide universal and/or nearly-universal attachment of the bottle or other receptacle to the breast pump shield 100. It therefore should be understood that the above-described examples are illustrative and therefore should not be construed as being limiting in any way.

FIG. 10 shows the thread attachment mechanism 900 in additional detail. In particular, FIG. 10 is an expanded view of a portion of the thread attachment mechanism 900, as viewed at the view circle C in FIG. 9. It should be understood that this example is illustrative and therefore should not be construed as being limiting in any way.

The thread attachment mechanism 900 can include a body 1002. The body 1002 can be formed by cutting material from the main body portion to create a gap 1004. Thus, the body 1002 can be formed at as a separate piece (relative to the remainder of the body portion 102) and/or can be formed from the body portion 102. It should be understood that these examples are illustrative and therefore should not be construed as being limiting in any way.

In the illustrated embodiment, the body 1002 is formed as a separate piece and joined to the body portion 102 to provide the functionality associated with the thread attachment mechanism 900. With collective reference to FIGS. 9-11, the structure of the thread attachment mechanism 900 will be described in additional detail.

In the illustrated embodiment, the thread attachment mechanism 900 includes a pin insertion structure 1006. A pin, axle, or other structure ("pin") 1008 can be inserted through the pin insertion structure 1006 and held in place by a portion of the body 1002. Thus, the body 1002 of the thread attachment mechanism 900 can rotate about an axis formed by the pin 1008, e.g., through a center of the pin insertion structure 1006 and/or an aperture formed therein. It should be understood that this example is illustrative and therefore should not be construed as being limiting in any way.

The thread attachment mechanism 900 also can include a thread engagement tooth 1010 and/or two or more thread engagement teeth 1010. The thread engagement tooth 1010 can be configured to engage a thread of a bottle (e.g., a baby bottle). Thus, some embodiments of the thread attachment mechanism 900 can provide a structure that can engage male threads of a bottle instead of including female threads on the inside of the body 1002. It should be understood that this example is illustrative and therefore should not be construed as being limiting in any way.

In particular, the thread engagement tooth 1010 (and/or combination of two or more thread engagement teeth 1010) can be configured to pass over male threads of a bottle or other container (e.g., by spring loading the body 1002 such that the engagement tooth 1010 can move over the threads via rotation of the thread engagement teeth 1010 via rotation of the body 1002 about the axis or pin 1008 as will be appreciated with reference to the FIGURES). After the thread engagement teeth 1010 passes over the threads of the bottle, the body 1002 can rotate back into position and an engagement surface 1012 of the thread engagement teeth 1010 can engage the threads of the bottle or other container, thereby holding the bottle or other container in position to receive milk from the breast pump shield 100 without requiring screwing of the bottle or other container into the body portion 102. It should be understood that this example is illustrative and therefore should not be construed as being limiting in any way.

The body 1002 of the thread attachment mechanism 900 also can include finger grips 1014 and/or a spring 1016, as can be appreciated from the description above. As can be seen in FIGS. 9-10, a ledge 1018 can be formed in the body 1002 to provide a surface against which the spring 1016 can work, if desired. It should be understood that this example is illustrative and therefore should not be construed as being limiting in any way.

As such, various embodiments of the concepts and technologies described herein can provide a universal attachment (and/or nearly universal attachment) for the breast pump shield 100 for either milk bags and/or bottles. It should be understood that this example is illustrative and therefore should not be construed as being limiting in any way.

Figure 12A:
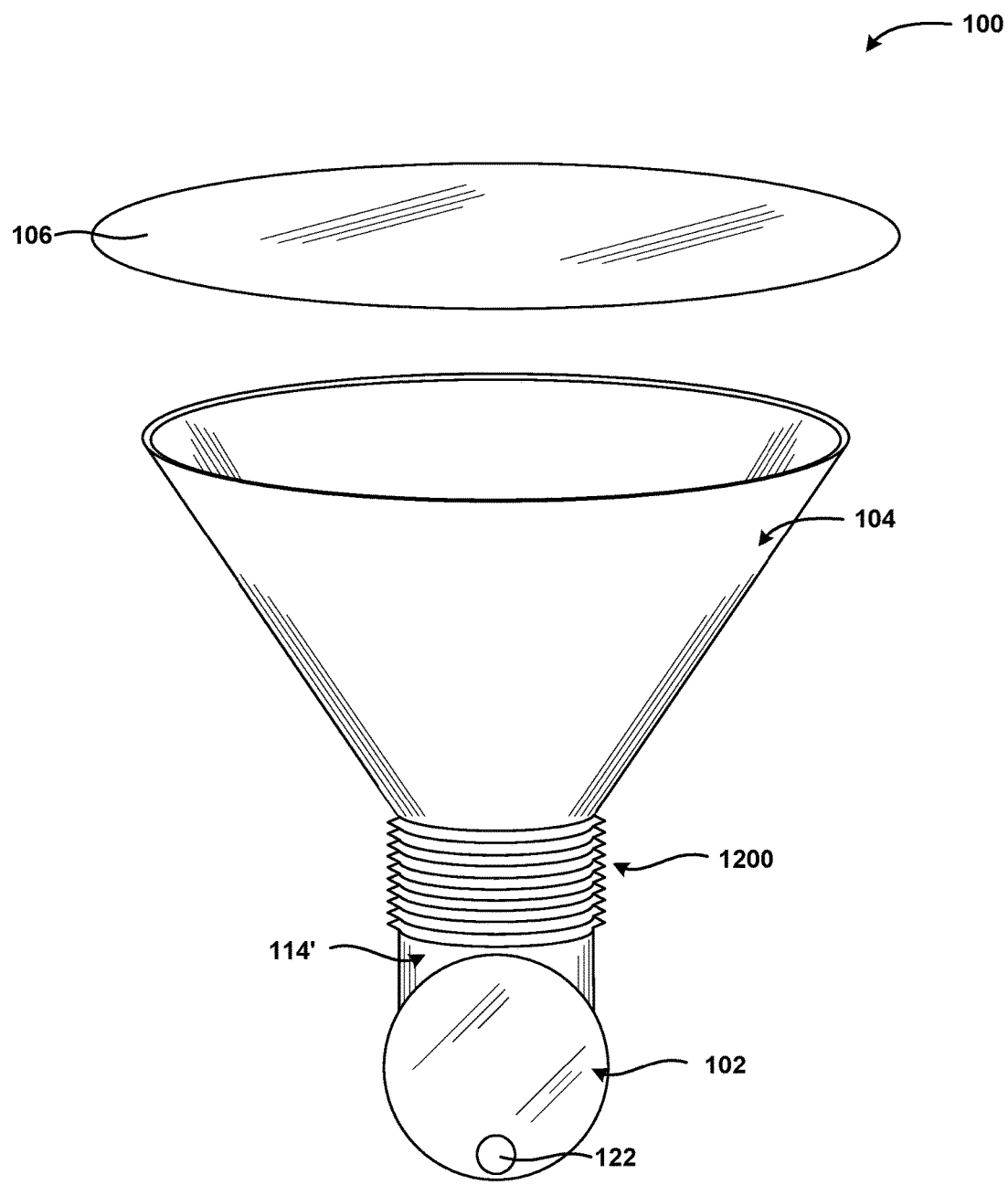
FIGS. 12A-12B are line drawings illustrating top elevation views of a breast pump shield, according to another illustrative embodiment of the concepts and technologies described herein.
Figure 12B:
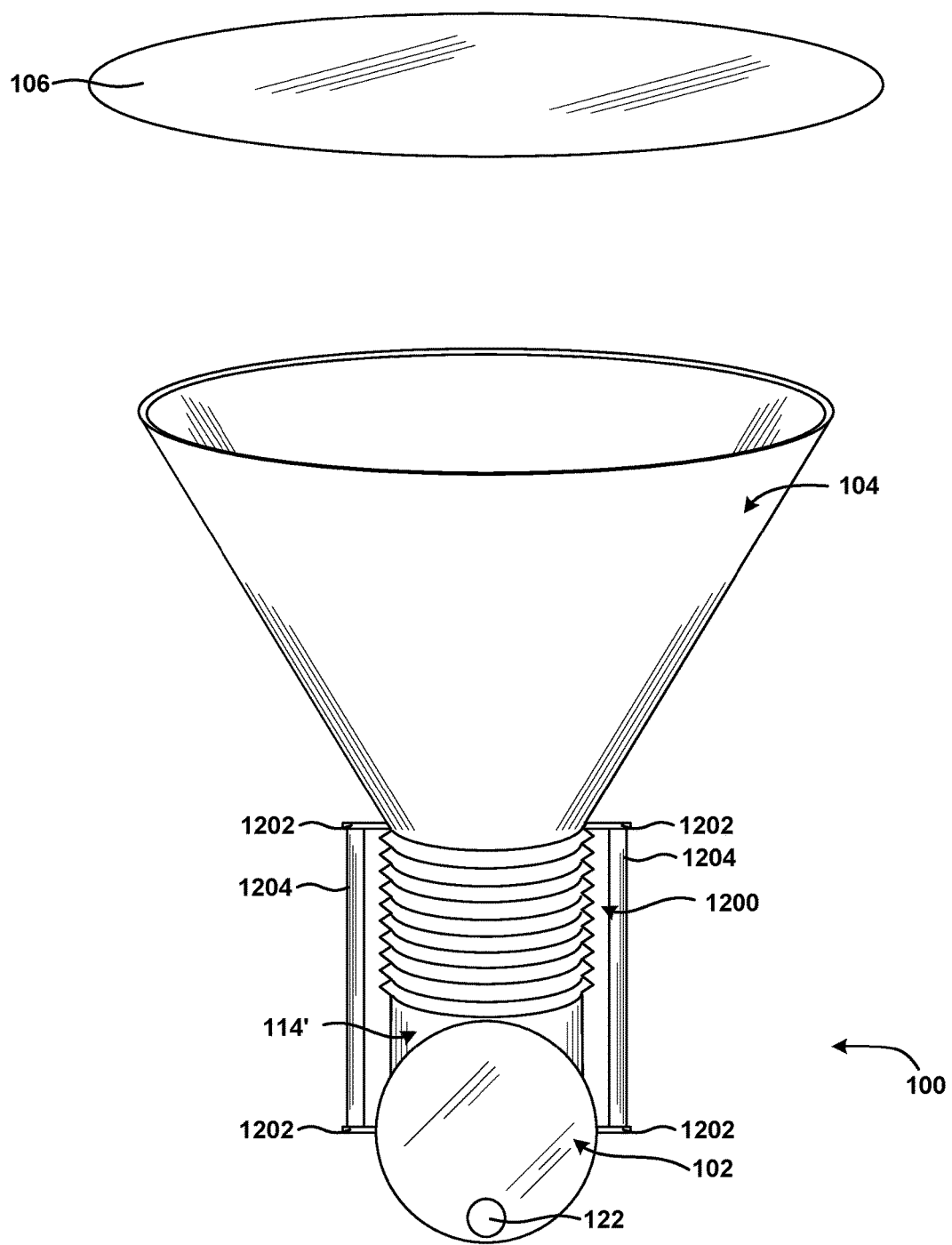

Turning to FIGS. 12A-12B, additional details of the breast pump shield 100 are illustrated and described in detail. In particular, FIGS. 12A-12B are line drawings illustrating top elevation views of a breast pump shield 100, according to another illustrative embodiment of the concepts and technologies described herein. Because the various components of the breast pump shield 100 can be arranged in various configurations, it should be understood that the views shown in FIGS. 12A-12B could also correspond to side elevation views and/or bottom elevation views instead of, or in addition to, top elevation views.

As shown in FIG. 12A, some embodiments of the breast pump shield 100 can include an expandable and/or collapsible funnel insertion portion 114'. In various embodiments, the expandable and/or collapsible funnel insertion portion 114' can include an expandable and collapsible ridged portion (hereinafter referred to as a "ridged portion") 1200. The ridged portion 1200 can be collapsed or expanded based on desires or needs of a user. In the embodiment shown in FIG. 12A, the ridged portion 1200 of the collapsible funnel insertion portion 114' is illustrated as being collapsed, while in FIG. 12B, ridged portion 1200 of the collapsible funnel insertion portion 114' is illustrated as being expanded. In some embodiments, the funnel portion 104 can be formed as part of (or an extension of) the collapsible funnel insertion portion 114' instead of being formed as two pieces as illustrated and described herein. It should be understood that these examples are illustrative and therefore should not be construed as being limiting in any way.

In some embodiments, the ridged portion 1200 can be included on the breast pump shield 100 to collapse the breast pump shield 100, at least partially, to make the size of the breast pump shield 100 compact. Thus, when the ridged portion 1200 is collapsed, the breast pump shield 100 may consume less space in a diaper bag, glove compartment, purse, or other area for convenience. In some embodiments, the ridged portion 1200 also can be used to protect the lubricant layer 500, 604. In particular, the ridges of the ridged portion 1200 can be used to hold or retain the lubricant used to provide the lubricant layer 500, 604 at a desired location. It should be understood that this example is illustrative and therefore should not be construed as being limiting in any way.

In some embodiments, an example of which is shown in FIG. 12B, the breast pump shield 100 can include support structures such as the supports 1202 and the support rods 1204. According to various embodiments, the supports 1202 and/or the rods 1204 can be formed from plastics, metals, alloys, thermoplastics, acrylics, epoxies and/or resins, wood, glass, and/or other materials. The support structures can be used to hold the breast pump shield 100 in a configuration at which the ridged portion 1200 is expanded. It can be appreciated that the suction generated by the breast pump (whether manual or electronic) can be sufficient to collapse the ridged portion 1200, which can reduce the realized suction at the nipples of the user. Thus, some embodiments such as the example shown in FIG. 12B include the support structures. In some embodiments, the rods 1204 can be removable and/or reusable. As such, the rods 1204 can be removed, and the ridged portion 1200 can be collapsed, if desired.

Although not visible in the FIGURES, some embodiments of the concepts and technologies described herein include additional supports 1202 and rods 1204. In particular, supports can be located near the beginning of the collapsible funnel insertion portion 114'. Thus, some embodiments of the concepts and technologies described herein can make use of collapsible and/or soft or semi-soft materials for the body portion 102. A collapsible or semi-collapsible body portion 102 can be provided with support by the supports 1202 and rods 1204. It should be understood that these examples are illustrative and therefore should not be construed as being limiting in any way.

According to various embodiments of the concepts and technologies described herein, the breast pump shield 100 is configured to provide a universal or nearly-universal disposable breast pump shield 100 that can be used with various brands of breast pumps. Thus, the breast pump shield 100 can be used by almost any user, regardless of what brand and/or model breast pump the user owns and/or uses. It should be understood that various modifications can be made to the threads, thread attachment mechanisms 900, hooks 130, and/or other structures to realize this goal of providing a universal and/or nearly universal breast pump shield 100.

According to some embodiments of the concepts and technologies described herein, the breast pump shield 100 can be offered in various sizes and/or options. Additionally, or alternatively, the funnel portions 104 can be provided in various sizes and/or models that can provide various options. In some embodiments, for example, the funnel portions 104 can be offered in smooth and/or ribbed configurations, depending upon users' preferences. It should be understood that these examples are illustrative and therefore should not be construed as being limiting in any way.

In some contemplated embodiments, the breast pump shield 100 and/or portions thereof (e.g., the body portion 102, the funnel portion 104, and/or other portions) can be formed from glow in the dark materials. These embodiments can be useful for mothers and/or other users (e.g., healthcare professionals) during the night and/or in other low-light conditions. It should be understood that this example is illustrative and therefore should not be construed as being limiting in any way.

Based on the foregoing, it should be appreciated that embodiments of a disposable breast pump shield have been disclosed herein. Although the subject matter presented herein has been described in conjunction with one or more particular embodiments and implementations, it is to be understood that the embodiments defined in the appended claims are not necessarily limited to the specific structure, configuration, or functionality described herein. Rather, the specific structure, configuration, and functionality are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the embodiments, which is set forth in the following claims.

I claim:

1. A breast pump shield comprising:
a body portion comprising a breast engagement portion and a neck portion that is located at a first end of the body portion, wherein the breast engagement portion comprises a ring that is located at a second end of the body portion, wherein the breast engagement portion is configured to receive least a portion of a human breast, and wherein the neck portion is configured to receive at least a portion of a nipple of the human breast and to receive milk from the human breast;
a suction chamber that is located in proximity to the neck portion, wherein the suction chamber comprises a funnel insertion portion that is configured to receive the body portion;
a hook located on the body portion; and
a cover located at the ring of the body portion, wherein the cover comprises a support layer and a lubricant layer, wherein the support layer has a first side and a second side, wherein the lubricant layer is located at the first side of the support layer, wherein the lubricant layer comprises a lubricant, and wherein the support layer cooperates with the body portion to provide at least part of a hermetic seal for the breast pump shield prior to use.

2. The breast pump shield of claim 1, wherein the lubricant comprises a food grade lubricant.

3. The breast pump shield of claim 2, wherein the food grade lubricant comprises at least one lubricant selected from a group of lubricants consisting of:
a coconut-based lubricant; and
a vegetable-based lubricant.

4. The breast pump shield of claim 1, wherein the breast pump shield is disposable.

5. The breast pump shield of claim 4, wherein the lubricant comprises at least one lubricant selected from a group of lubricants consisting of:
a mineral-oil based lubricant;
a petroleum-based lubricant; and
a shea-based lubricant.

6. The breast pump shield of claim 1, wherein the cover further comprises a wiping layer located at the second side of the support layer.

7. The breast pump shield of claim 6, wherein the wiping layer is formed from a cotton-based fabric.

8. The breast pump shield of claim 1, wherein the cover further comprises a wiping layer located at the second side of the support layer, wherein the breast pump shield is disposable, wherein a further lubricant layer is located within the breast engagement portion, the neck portion, and the suction chamber, and wherein a further cover is located over an inlet formed in the suction chamber.

9. The breast pump shield of claim 1, wherein the support layer is formed from a metal foil, and wherein the support layer prevents leakage of the lubricant layer from the breast pump shield.

10. The breast pump shield of claim 1, wherein the hook is configured to hold a milk bag in a position at which the milk bag receives milk from the suction chamber.

11. The breast pump shield of claim 1, wherein the hook is configured to hold a bottle in a position at which the bottle receives milk from the suction chamber.

12. The breast pump shield of claim 1, further comprising another hook, wherein the hook and the other hook are configured to hold a milk bag in a position at which the milk bag receives milk from the suction chamber.

13. A breast pump shield comprising:
a body portion comprising a breast engagement portion and a neck portion that is located at a first end of the body portion, wherein the breast engagement portion comprises a ring that is located at a second end of the body portion, wherein the breast engagement portion is configured to receive at least a portion of a human breast of a user, and wherein the neck portion is configured to receive at least a portion of a nipple of the user and to receive milk from the human breast;
a suction chamber comprising a funnel insertion portion that is configured to receive at least a portion of the neck portion, the suction chamber comprising an inlet;
a hook located on the body portion;
and a first cover located at the ring of the body portion, wherein the first cover comprises a support layer, a lubricant layer, and a wiping layer, wherein the support layer comprises a first side and a second side, wherein the lubricant layer is located at the first side of the support layer, wherein the lubricant layer comprises a lubricant, wherein the wiping layer is located at the second side of the support layer, wherein the first cover cooperates with the body portion to provide at least part of a hermetic seal for an interior space of the body portion prior to use, and wherein the breast pump shield is disposable.

14. The breast pump shield of claim 13, wherein the lubricant comprises a food grade lubricant selected from a group of lubricants consisting of:
a coconut-based lubricant;
a flax-seed-based lubricant;
a fish-oil-based lubricant; and
a vegetable-based lubricant.

15. The breast pump shield of claim 13, wherein the lubricant is selected from a group of lubricants consisting of:
a mineral-oil based lubricant;
a petroleum-based lubricant; and
a shea-based lubricant.

16. The breast pump shield of claim 13,
wherein a further lubricant layer is located within the body portion, the neck portion, and the suction chamber, and
wherein a second cover is located over the inlet.

17. The breast pump shield of claim 16, further comprising:
an assembly structure for connecting the breast pump shield to a bottle; and
a third cover located at the assembly structure.

18. The breast pump shield of claim 13, further comprising another hook, wherein the hook and the other hook are configured to hold a milk bag in a position at which the milk bag receives milk from the suction chamber.

19. A breast pump shield comprising:
a body portion comprising a breast engagement portion and a neck portion, wherein the breast engagement portion comprises a ring, wherein the breast engagement portion is configured to receive at least a portion of a human breast of a user, and wherein the neck portion is configured to receive at least a portion of a nipple of the user and to receive milk from the human breast;
a suction chamber located in proximity to the neck portion, the suction chamber comprising an inlet through which a breast pump is connected to the suction chamber;
a cover located at the ring of the body portion;
two hooks located on the body portion, wherein the hooks are configured to hold a milk bag in a position at which the milk bag receives milk from the suction chamber; and
wherein the cover comprises a support layer; a lubricant layer located at a first side of the support layer; and a wiping layer located at a second side of the support layer, wherein the cover cooperates with the body portion to provide at least part of a hermetic seal for an interior space of the body portion prior to use, wherein the lubricant layer comprises a lubricant, and wherein the breast pump shield is disposable and configured for disposal after one use.

20. The breast pump shield of claim 19,
wherein a further lubricant layer is located within the body portion, the neck portion, and the suction chamber,
wherein a further cover is located over the inlet, and
wherein the lubricant is selected from a group of lubricants consisting of:
a coconut-based lubricant;
a flax-seed-based lubricant;
a fish-oil-based lubricant;
a vegetable-based lubricant;
a mineral-oil based lubricant;
a petroleum-based lubricant; and
a shea-based lubricant.

* * * * *